(12) United States Patent
Wu et al.

(10) Patent No.: US 10,549,121 B2
(45) Date of Patent: Feb. 4, 2020

(54) AUTOMATIC DETERMINATION OF RADIATION BEAM CONFIGURATIONS FOR PATIENT-SPECIFIC RADIATION THERAPY PLANNING

(71) Applicants: Duke University, Durham, NC (US); The University of North Carolina at Charlotte, Charlotte, NC (US)

(72) Inventors: Qingrong Jackie Wu, Durham, NC (US); Yaorong Ge, Matthews, NC (US); Fang-Fang Yin, Durham, NC (US); Lulin Yuan, Durham, NC (US)

(73) Assignees: Duke University, Durham, NC (US); The University of North Carolina at Charlotte, Charlotte, NC (US)

( * ) Notice: Subject to any disclaimer, the term of this patent is extended or adjusted under 35 U.S.C. 154(b) by 240 days.

(21) Appl. No.: 15/555,489

(22) PCT Filed: Mar. 7, 2016

(86) PCT No.: PCT/US2016/021272
§ 371 (c)(1),
(2) Date: Sep. 1, 2017

(87) PCT Pub. No.: WO2016/144915
PCT Pub. Date: Sep. 15, 2016

(65) Prior Publication Data
US 2018/0043184 A1 Feb. 15, 2018

Related U.S. Application Data

(60) Provisional application No. 62/129,102, filed on Mar. 6, 2015.

(51) Int. Cl.
*A61N 5/10* (2006.01)

(52) U.S. Cl.
CPC ......... *A61N 5/1038* (2013.01); *A61N 5/1031* (2013.01); *A61N 5/1039* (2013.01);
(Continued)

(58) Field of Classification Search
CPC .............. A61N 5/103–1039; A61N 2005/1041
See application file for complete search history.

(56) References Cited

U.S. PATENT DOCUMENTS

| 6,327,490 B1 | 12/2001 | Spetz |
| 2002/0080915 A1 | 6/2002 | Frohlich |

(Continued)

FOREIGN PATENT DOCUMENTS

| EP | 3384959 A1 | 10/2018 |
| WO | 03011390 A2 | 2/2003 |

OTHER PUBLICATIONS

Decision of Rejection issued in counterpart Chinese Application No. 201480034786.7 dated Jul. 6, 2018 (five (5) pages).

(Continued)

*Primary Examiner* — Thaddeus B Cox
(74) *Attorney, Agent, or Firm* — Olive Law Group, PLLC

(57) ABSTRACT

Systems and methods for efficient and automatic determination of radiation beam configurations for patient-specific radiation therapy planning are disclosed. According to an aspect, a method includes receiving data based on patient information and geometric characterization of one or more organs at risk proximate to a target volume of a patient. The method includes determining automatically one or more radiation treatment beam configuration sets. Further, the method includes presenting the determined one or more radiation beam configuration sets via a user interface.

22 Claims, 8 Drawing Sheets

(52) U.S. Cl.
CPC .... *A61N 5/1077* (2013.01); *A61N 2005/1041* (2013.01); *A61N 2005/1074* (2013.01)

(56) References Cited

U.S. PATENT DOCUMENTS

| | | |
|---|---|---|
| 2010/0208867 A1 | 8/2010 | Nord et al. |
| 2012/0014507 A1 | 1/2012 | Wu et al. |
| 2012/0226152 A1 | 9/2012 | Porikli |
| 2013/0034050 A1 | 2/2013 | Ros et al. |
| 2013/0090549 A1 | 4/2013 | Meltsner et al. |
| 2013/0197878 A1 | 8/2013 | Fiege et al. |
| 2014/0350863 A1 | 11/2014 | Hartman et al. |
| 2016/0129282 A1 | 5/2016 | Yin et al. |
| 2017/0173365 A1* | 6/2017 | Bzdusek ............... A61N 5/103 |
| 2017/0259082 A1* | 9/2017 | Bzdusek ............... A61N 5/103 |

OTHER PUBLICATIONS

Communication Pursuant to Rule 69 EPC issued in counterpart EP Application No. 18170881 dated Oct. 15, 2018 (two (2) pages).

Non-Final Office Action issued in counterpart U.S. Appl. No. 14/893,055 dated Jan. 11, 2019.

Extended European Search Report issued in counterpart EP Application No. 18170881.9 dated Jun. 29, 2018, (five (5) pages).

Non-Final Office Action issued in counterpart U.S. Appl. No. 15/555,488 dated Mar. 22, 2019.

Final Office Action issued in counterpart U.S. Appl. No. 14/893,055 dated Sep. 10, 2018.

Appenzoller L M, Michalski J M, Thorstad W L, Mutic S and Moore K L 2012 Predicting dose-volume histograms for organs-at-risk in IMRT planning Med Phys. 39 7446-61.

Wang X, Zhang X, Dong L, Liu H, Gillin M, Ahamad A, Ang K and Mohan R 2005 Effectiveness of noncoplanar IMRT planning using a parallelized multiresolution beam angle optimization method for paranasal sinus carcinoma Int J Radiat Oncol Biol Phys 63 594-601.

Chanyavanich V, Das S K, Lee W R and Lo J Y 2011 Knowledge-based IMRT treatment planning for prostate cancer Med Phys. 38 2515-22.

Cootes T F, Edwards G J and Taylor C J 2001 Active appearance models IEEE Transactions on Pattern Analysis and Machine Intelligence 23 681-5.

Cootes T F, Taylor C J, Cooper D H and Graham J 1995 Active Shape Models—Their Training and Application Computer Vision and Image Understanding 61 38-59.

Heimann T and Meinzer H-P 2009 Statistical shape models for 3D medical image segmentation: A review Medical Image Analysis 13 543-63.

Shirvani S M, Juloori A, Allen P K, Komaki R, Liao Z, Gomez D, O'Reilly M, Welsh J, Papadimitrakopoulou V, Cox J D and Chang J Y 2013 Comparison of 2 common radiation therapy techniques for definitive treatment of small cell lung cancer Int J Radiat Oncol Biol Phys 87 139-47.

Schreibmann E and Xing L 2004 Feasibility study of beam orientation class-solutions for prostate IMRT Medical Physics 31 2863.

Pugachev A, Li J G, Boyer A L, Hancock S L, Le Q T, Donaldson S S and Xing L 2001 Role of beam orientation optimization in intensity-modulated radiation therapy Int J Radiat Oncol Biol Phys 50 551-60.

Liao Z X, Komaki R R, Thames H D, Jr., Liu H H, Tucker S L, Mohan R, Martel M K, Wei X, Yang K, Kim E S, Blumenschein G, Hong W K and Cox J D 2010 Influence of technologic advances on outcomes in patients with unresectable, locally advanced non-small-cell lung cancer receiving concomitant chemoradiotherapy Int J Radiat Oncol Biol Phys 76 775-81.

Lee K J, Barber D C and Walton L 2006 Automated gamma knife radiosurgery treatment planning with image registration, data-mining, and Nelder-Mead simplex optimization. Med Phys. 33 2532-40.

Lian J, Yuan L, Ge Y, Chera B S, Yoo D P, Chang S, Yin F-F and Wu Q J 2013 Modeling the dosimetry of organ-at-risk in head and neck IMRT planning: an intertechnique and interinstitutional study Med Phys. 40 121704.

Moore K L, Brame R S, Low D A and Mutic S 2011 Experience-based quality control of clinical intensity-modulated radiotherapy planning Int J Radiat Oncol Biol Phys. 81 545-51.

Rueckert D, Frangi A F and Schnabel J A 2003 Automatic construction of 3-D statistical deformation models of the brain using nonrigid registration IEEE Trans Med Imaging. 22 1014-25.

Sahgal A, Ma L, Gibbs I, Gerszten P C, Ryu S, Soltys S, Weinberg V, Wong S, Chang E, Fowler J and Larson D A 2010 Spinal cord tolerance for stereotactic body radiotherapy International journal of radiation oncology, biology, physics 77 548-53.

Wu B, McNutt T, Zahurak M, Simari P, Pang D, Taylor R and Sanguineti G 2012 Fully Automated Simultaneous Integrated Boosted-Intensity Modulated Radiation Therapy Treatment Planning Is Feasible for Head-and-Neck Cancer: A Prospective Clinical Study International Journal of Radiation Oncology Biology Physics 84 647-53.

Wu B, Ricchetti F, Sanguineti G, Kazhdan M, Simari P, Chuang M, Taylor R, Jacques R and McNutt T 2009 Patient geometry-driven information retrieval for IMRT treatment plan quality control Med. Phys. 36 5497-505.

Yasushi, H., Kataoka, M., Senba, T., Uwatsu, K., Sugawara, Y., Inoue, T., Sakai, S., Aono, S., Takahashi, T. and Oda, S.: Vertebral Metastases with High Risk of Symptomatic Malignant Spinal Cord Compression. Japanese Journal of Clinical Oncology, 39(7), 431-434 (2009).

Yuan L, Ge Y, Lee W R, Yin F F, Kirkpatrick J P and Wu Q J 2012 Quantitative analysis of the factors which affect the interpatient organ-at-risk dose sparing variation in IMRT plans Med Phys. 39 6868-78.

Yuan L, Wu Q J, Yin F-F, Jiang Y, Yoo D P and Ge Y 2014 Incorporating single-side sparing in models for predicting parotid dose sparing in head and neck IMRT Med. Phys. 41 021728.

Zhang Z 1994 Iterative point matching for registration of free-form curves and surfaces International Journal of Computer Vision 13 119-52.

Zhu X, Ge Y, Li T, ThongPhiew D, Yin F-F and Wu Q J 2011 A planning quality evaluation tool for prostate adaptive IMRT based on machine learning Med Phys. 38 719-26.

Jonker R and Volgenant A 1987 A Shortest Augmenting Path Algorithm for Dense and Sparse Linear Assignment Problems Computing 38 325-40.

Zhang H H, Gao S, Chen W, Shi L, D'Souza W D and Meyer R R 2013 A surrogate-based metaheuristic global search method for beam angle selection in radiation treatment planning Phys Med Biol 58 1933-46.

Zhang, X. Li, X. Quan, E.M. and Li, Y.: A methodology for automatic intensity-modulated radiation treatment planning for lung cancer. Physics in Medicine and Biology. 56(13), 3873-3893 (2011).

Jia X, Men C, Lou Y and Jiang S B 2011 Beam orientation optimization for intensity modulated radiation therapy using adaptive I(2,1)-minimization Phys Med Biol 56 6205-22.

Ji K, Zhao L J, Liu W S, Liu Z Y, Yuan Z Y, Pang Q S, Wang J and Wang P 2014 Simultaneous integrated boost intensity-modulated radiotherapy for treatment of locally advanced non-small-cell lung cancer: a retrospective clinical study The British journal of radiology 87 20130562.

Harris J P, Murphy J D, Hanlon A L, Le Q T, Loo B W, Jr. and Diehn M 2014 A Population-Based Comparative Effectiveness Study of Radiation Therapy Techniques in Stage III Non-Small Cell Lung Cancer Int J Radiat Oncol Biol Phys 88 872-84.

Das S, Cullip T, Tracton G, Chang S, Marks L, Anscher M and Rosenman J 2003 Beam orientation selection for intensity-modulated radiation therapy based on target equivalent uniform dose maximization Int J Radiat Oncol Biol Phys 55 215-24.

Craft D 2007 Local beam angle optimization with linear programming and gradient search Phys Med Biol 52 N127-35.

Breedveld S, Storchi P R, Voet P W and Heijmen B J 2012 iCycle: Integrated, multicriterial beam angle, and profile optimization for generation of coplanar and noncoplanar IMRT plans Med Phys 39 951-63.

(56) References Cited

OTHER PUBLICATIONS

Abraham C, Molinari N and Servien R 2013 Unsupervised clustering of multivariate circular data Statistics in Medicine 32 1376-82.
International Search Report and Written Opinion issued in PCT Application No. PCT/US2016/021272 dated Jun. 10, 2016.
Decision to Grant a European Patent Pursuant to Article 97(1) EPC issued in counterpart EP Application No. 14813397.8 dated Apr. 12, 2018. (two (2) pages).
International Preliminary Report on Patentability and Written Opinion issued in PCT Application No. PCT/US16/063204 dated May 22, 2018, (six (6) pages).
Communication under Rule 71(3) EPC issued in counterpart EP Application No. 18 170 881.9 dated May 21, 2019 (101 pages).
Notice of Allowance issued in counterpart U.S. Appl. No. 14/893,055 dated Jun. 7, 2019.
Chinese-language Office Action issued in counterpart Chinese Application No. 201480034786.7 dated Sep. 20, 2017 with English translation (eight (8) pages).
International Report on Patentability for PCT Application No. PCT/US2016/021272 dated Sep. 12, 2017 (six (6) pages).
Office Action issued in counterpart CN Application No. 201480034786.7 dated Mar. 8, 2018.
Non-Final Office Action issued in counterpart U.S. Appl. No. 14/893,055 dated Mar. 22, 2018.
Notification of Re-examination issued in counterpart Chinese application No. 201480034786.7 dated Jun. 28, 2019 (six (6) pages).
Supplemental Notice of Allowability issued in counterpart U.S. Appl. No. 14/893,055 dated Aug. 7, 2019.
Supplemental Notice of Allowability issued in counterpart U.S. Appl. No. 14/893,055 dated Aug. 11, 2019.

\* cited by examiner

AUTOMATIC DETERMINATION OF RADIATION BEAM CONFIGURATIONS FOR PATIENT-SPECIFIC RADIATION THERAPY PLANNING

CROSS REFERENCE TO RELATED APPLICATIONS

This is a 371 national stage patent application, which claims priority to PCT International Patent Application No. PCT/US2016/021272, filed Mar. 7, 2016, and titled AUTOMATIC DETERMINATION OF RADIATION BEAM CONFIGURATIONS FOR PATIENT-SPECIFIC RADIATION THERAPY PLANNING, which claims the benefit of and priority to U.S. Provisional Patent Application Number 62/129,102, filed Mar. 6, 2015and titled SYSTEMS AND METHODS FOR EFFICIENT AND AUTOMATIC DETERMINATION OF RADIATION BEAM CONFIGURATION FOR PATIENT-SPECIFIC RADIATION THERAPY PLANNING; the disclosures of which are incorporated herein by reference in their entireties.

This application is related to PCT International Application Number PCT/US2016/021271, filed simultaneously herewith and titled SYSTEMS AND METHODS FOR AUTOMATED RADIATION TREATMENT PLANNING WITH DECISION SUPPORT.

This application is related to U.S. patent application Ser. No. 14/893,055, titled SYSTEMS AND METHODS FOR SPECIFYING TREATMENT CRITERIA AND TREATMENT PARAMETERS FOR PATIENT SPECIFIC RADIATION THERAPY PLANNING and filed Nov. 21, 2015.

FEDERALLY SPONSORED RESEARCH OR DEVELOPMENT

The present disclosure was made partially with Government Support under Federal Grant No. R21CA161389 awarded by the National Institute of Health (NIH). The Government has certain rights to this invention.

TECHNICAL FIELD

The presently disclosed subject matter relates to radiation treatment planning. Particularly, the presently disclosed subject matter relates systems and methods for efficiently and automatically determining beam configurations specialized to a patient's unique anatomical and clinical conditions.

BACKGROUND

Radiation treatment planning involves complex decision making in specifying the best possible treatment criteria and designing treatment parameters that take into account all aspects of patient conditions and treatment constraints. When physicians specify the best possible treatment criteria that includes the prescription to the target, dose sparing criteria for each of the critical organs at risk (OARs), they combine their personal experience and knowledge, published guidelines, and patient's specific condition into numerical specifications for the radiation treatment to be designed. For the given treatment criteria, physicians and planners try to design a treatment plan that can best possibly meet these criteria. The design includes a set of parameters, such as beam angles, beam ranges, beam energies, beam sizes, dose limits or volume limits, and associated priorities for sparing various organs or anatomy structures, that can be used in determining the treatment plan and the treatment dose distribution. Once the parameters that best meet the treatment criteria are determined, a high quality treatment plan can be manually or automatically generated that leads to highest quality radiation treatment for the specific patient. For cases in the thorax, abdomen and upper pelvic, as well as the brain, the selection of the incident angles of the treatment beams is a critical component of designing planning parameters. Current practice of selection of best beam angles or beam ranges for a specific case largely relies on personal experience and knowledge.

Previous techniques include methods for beam configuration determination. These techniques can be divided into three approaches. In one approach, one or more beam configuration templates (beam bouquets) are determined from prior clinical plans and are then applied to new cases that fit the general characteristics of the tumor (such as location, cancer type, and the like). This approach leverages prior expert knowledge and experience, but does not consider unique information of the new patient. In the second approach, physics-based principles and anatomical information are used to find the most efficient beam pathways in the existence of tumor and critical organs. These solutions leverage unique anatomical information of a new patient, they are efficient, but they rely on some fixed, general assumptions that may not cover all clinical needs. In the third approach, direct dose optimization methods, such as simulated annealing, genetic algorithm, sparse optimization, nested partition, pattern search and column generation are used to determine a set of individual beam angle positions. These solutions can be computationally very expensive and therefore often require heuristic approximations. For example, two of the previous solutions choose to iteratively add or subtract one beam at a time until a local optimum is reached. The subtraction method starts with a set of most frequently used beams determined from a collection of prior plans. Most of these previous solutions do not handle non-coplanar beam angles and do not consider prior knowledge.

For the aforementioned reasons, current practice of selection of best beam angles or beam ranges for a specific case largely relies on personal experience and knowledge. Thus, there is a desire to provide systems and techniques that can efficiently and automatically determine beam configurations that are not only based on the best available clinical experience and knowledge but also specialized to a patient's unique anatomical and clinical conditions.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present disclosure provides, in part, a novel beam configuration determination method that utilizes both data-driven knowledge and physics principle driven mathematic models. This unique system also takes into consideration of patient's specific physiological conditions, physician's dose prescriptions and organ sparing goals, and collectively reaches a beam configuration that best suit the patient's case. This technique is automatic and predictive rather than iterative, as the trial-and-add, or trial-and-eliminate method, where the beam configuration is derived from the models. This technique also differs from previous method, as it is model-driven versus template-driven. Furthermore, this novel technique incorporates non-coplanar beam angles that can improve plan quality.

Disclosed herein are systems and methods for efficient and automatic determination of radiation beam configurations for patient-specific radiation therapy planning that effectively incorporate both coplanar and non-coplanar beam angles. According to an aspect, a method includes receiving data based on patient information and geometric characterization of one or more organs at risk proximate to a target volume of a patient. The method includes determining automatically one or more radiation treatment beam configuration sets. Further, the method includes presenting the determined one or more radiation beam configuration sets via a user interface.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1:
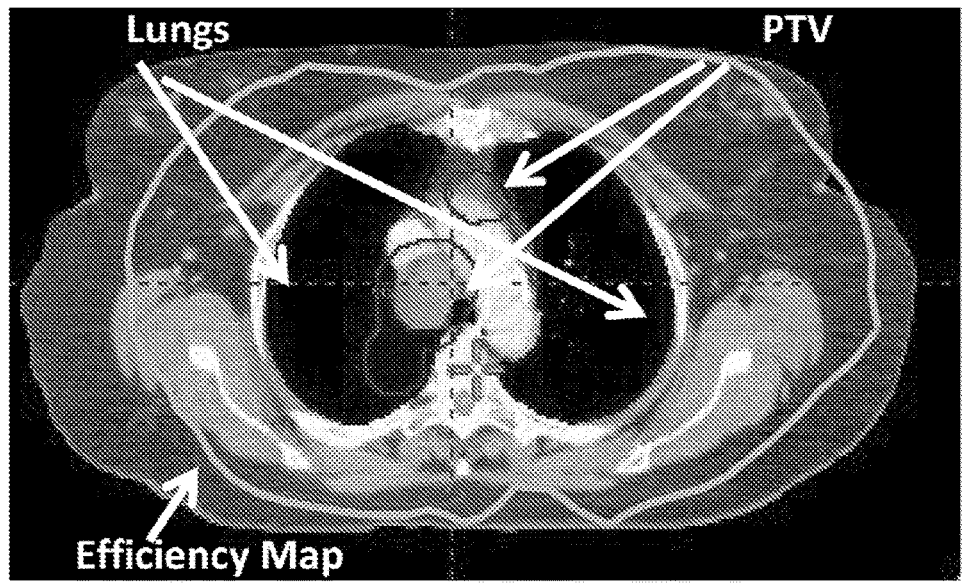
FIG. 1 is a beam angle efficiency map plotted on the CT image of example case.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

In accordance with embodiments of the present disclosure, systems and methods disclosed herein provide integrated computerized models of treatment beam angle selection based on patient's tumor anatomy, tumor dose prescription, organ dose sparing consideration, using the combined data-driven method that represent expert's knowledge in planning similar cases and physics principle-driven method that ensures patient anatomy variation and specific organ spraing goals can be precisely modeled. This system also combines prior data and knowledge and current patient data that determines the best beam configuration for the patient's radiation treatment.

In accordance with embodiments, the presently disclosed subject matter provides systems and methods for efficiently and automatically determining beam configurations specialized to a patient's unique anatomical and clinical conditions.

In accordance with embodiments, systems and methods disclosed herein can model an expert's knowledge on beam configuration by learning from databases of existing high-quality plans by expert planners, or by simulating high quality IMRT/VMAT plans using Pareto front plans generated by the multi-objective optimizations or similar systems. An assumption of the system and method is that, if all prior plans have been carefully designed to achieve a level of "best possible" coverage, then a new patient with a condition similar to those of a prior patient should be well served by the knowledge that went into the prior patient's plan.

In accordance with embodiments, the knowledge embedded in these plans that are extracted into beam configuration model are: 1) patient-specific anatomy (tumor target and its relationship to organs-at-risk, OARs), its extracted features, and their correlations to the dose distributions and dose features in the OARs, 2) beam configuration, its features, and their correlations to dose and dose features in the OARs. For VMAT, the beam configuration can be the span of the beam arc, defined as the starting and finishing beam position in a continuous radiation delivery mode, 3) physician's dose prescription and organ sparing objectives and considerations (including patient's specific physiological conditions, such as prior treatment, etc). The anatomy features about the patient include one or more of the following measures: PTV and OAR voxels and contours as defined by physician on the 3D CT/MR/PET images used for radiation treatment planning, OAR volumes, PTV volumes, fraction of OAR volumes that relate critical toxicity data point, distance to target histogram (DTH) in Euclidean system or other non-Euclidean metrics, distance of target to OAR histogram (DOH) in Euclidean system or other non-Euclidean metrics, the PTV center-of-mass coordinates. The dose features include one or more of following measures: PTV dose homogeneity, minimum and maximum dose, dose gradient around OAR and PTV, Partial dose gradient around one OAR, dose volume points (e.g., mean dose, median dose, max dose, dose corresponding to 30% volume, etc.) and dose volume histograms (DVH) of PTV and OAR, 3D isodose lines' positions and volumes, 3D isodose at specific anatomical points. The physicians prescription and its features include: dose prescription to the target or PTV, percentage of target to be covered, tradeoff preferences of dose coverage between target and OAR, tradeoff preferences of dose coverage/sparing among OARs, patients specific conditions, specific guidelines and numerical values used in dose prescription for target and OAR. The beam configuration and its features include: number of beams, beam orientation, beam start and ending position, beam orientations can be coplanar and non-coplanar.

In accordance with embodiments of the presently disclosed subject matter, the features of beam configurations in clinical plans can also be represented by a standard beam bouquet atlas. In embodiments, the atlas can be established by classifying the clinical plans into groups according to their beam configurations. In this embodiment, the beam arrangement in each method of the clusters is designated as the standardized beam bouquet for the cluster.

In accordance with embodiments, these features can be further processed to reduce dimension. For example, DVHs, DTHs, DOHs can be sent to dimension reduction techniques like principle component analysis to reduce the data dimension.

The knowledge model establishes the correlations using anatomical features, beam configuration features, and physician prescriptions as input and the dose features as output. Part or all of these features can be used at a time. The models can be trained with machine learning techniques and statistical analysis.

The anatomic features, dose features and physician prescription features represented in the groups (1) to (3) are formed as the input features and the beam configuration features in the group (4) are formed as output features.

The knowledge modeling process is the learning of the relationships of the input features and the output features. Once the model is trained, it can be used to predict the beam configuration of a new patient, given his/her unique anatomy and physician dose prescription and organ sparing objectives. Thus, the presently disclosed subject matter presents a model-driven beam configuration method.

One of learning method is to build a beam efficiency index for each possible beam position. A beam efficiency index (EI) $q_{\alpha v}$ is defined for potential beam angle $\alpha \in A$ and target voxel $v \in V$ as the ratio of the weighted sum of the dose deposited inside the OARs to the dose in the PTV along a ray originating from a target voxel and with directional angle $\alpha$.

The EI in the coplanar angle space forms a rose diagram, which is called a beam angle navigation map. The navigation map can be used to guide the selection of beam angles in IMRT/VMAT planning. Smaller values on the map indicate preferred beam directions. The beam angle efficiency map is a closed contour in 2D space (FIG. 1). FIG. 1 illustrates a beam angle efficiency map plotted on the CT image of example case.

Figure 2:
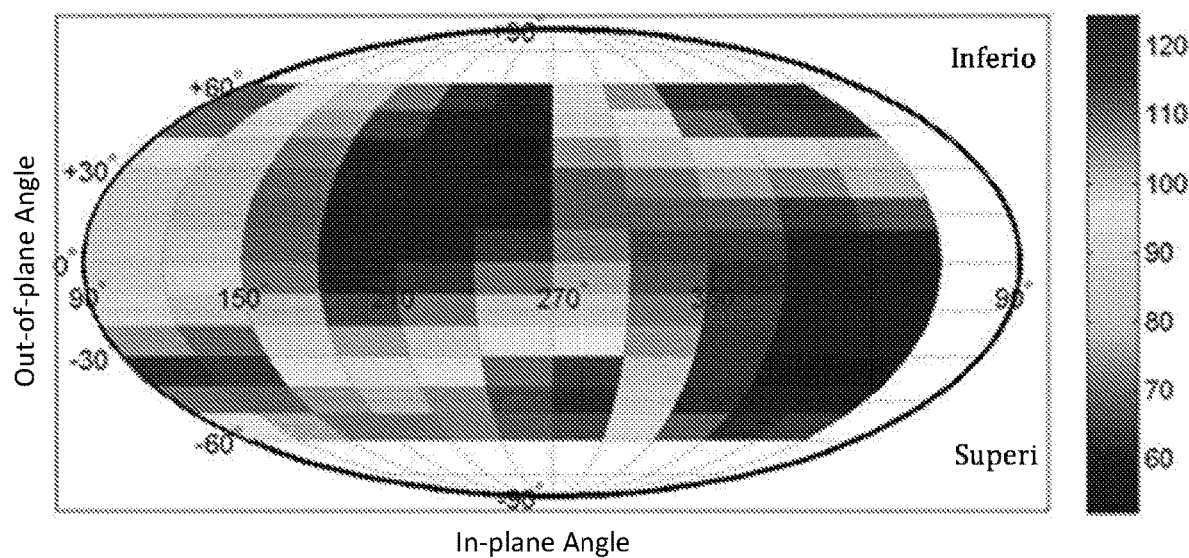
FIG. 2 illustrates a beam angle efficiency map for non-coplanar beam angles plot as Mollweide projection for an example case. It is color coded according to the color bar with arbitrary unit.

For non-coplanar angles, beam angle efficiency map can be visualized as a Mollweide projection on angle space (FIG. 2). FIG. 2 beam angle efficiency map for non-coplanar beam angles plot as Mollweide projection for an example case. FIG. 2 is greyscaled according to the greyscale bar.

One of the example format of the beam efficiency index (EI) $q_{\alpha v}$ can be written as weighted sum of the dose deposits in the voxels along the radiation beam's pathway:

$$q_{\alpha v}=(w_{NT} \cdot d_{NT}+w_{lung} \cdot d_{lung}+w_{heart} \cdot d_{heart}+w_{esoph} \cdot d_{esoph}+ w_{liver} \cdot d_{liver}+w_{stomach} \cdot d_{stomach}+w_{kidney} \cdot d_{kidney}+ w_{target} \cdot d_{target})/\max(d_{target}, C_{target})$$

where $d_{target}$, $d_{NT}$, $d_{lung}$, $d_{heart}$ and $d_{esoph}$, etc, are the doses delivered to the target volume, normal tissue, the lungs, heart, esophagus and other OARs, respectively. The w's is the weights for the sparing of the OARs and target coverage. The maximum function in the denominator is used to smooth the target dose $d_{target}$ when the rays pass through sharp edges on PTV contours. $C_{target}$ is the smoothing constant.

An example of the training the knowledge model is the learning of the weight w for different dose prescription objectives. The weights for different OARs and PTV represent the physician's dose prescription and dose sparing preferences among OARs. A higher weight indicates the dose sparing of that OAR has higher priority when choose beam orientations. Utilizing the OAR dose prediction method in our previous patent, these weights can be formalized as functions of the predictions of the dose-volume indices $d_i^{pred}$ and the physician's prescription $d_i^{cons}$:

$$w_i = \begin{cases} w_i^0 + k(d_i^{pred} - d_i^{cons}), & \text{when } d_i^{pred} > d_i^{cons} \\ w_i^0, & \text{when } d_i^{pred} < d_i^{cons} \end{cases}$$

where $w_i^0$ is the initial weight which is determined according to a universal template for a treatment site, k is a proportional constant. The formula indicates that when physician prescribes a dose constraint that is hard to be met, the beam configuration need to be chosen to achieve extra dose sparing for that OAR. The weights can also be adjusted iteratively and combined with adjustment of dose objectives priority. Further, the beam efficiency index $q\alpha$ for a candidate beam angle can be simplified by average the $q\alpha v$ among all the voxels on the PTV surface, combining all image slices.

$$q_\alpha = \Sigma_{v \in PTV} q_{\alpha v}$$

When the average EI map is used, often one set of beam configuration is designed per case.

Alternatively, each slice of the image slice can maintain its own map and different beam configurations can be used for different portions of the target. This is often necessary when target size is large and shape is complex, and the prescription dose impacts the multiple adjacent organs with different sparing preferences on different image slices.

In addition, the aforementioned features can be further processed to reduce dimension. For example, the center-of-mass coordinates can be used to represent the general position of the target, and the Fourier transformation can be applied to the EI map and its coefficients are extracted as the features representing the shape variation of the target. These features characterize the relative geometry of the tumor relative to the OARs as well as the tumor shapes.

The knowledge model can establish the correlations using anatomical features, beam configuration features, and physician prescriptions as input and the dose features as output. Part or all of these features can be used at a time. The models can be trained with machine learning techniques and statistical analysis.

As an example, a supervised clustering method can be used to train the model. In this model, the features of the beam efficiency index for each case are the explanatory variables and their beam configuration cluster assignments are response. A Naïve Bayesian classifier or support vector machine (SVM) can be used to train the cluster model.

Another example method to automatically select beam bouquet based on prior expert knowledge and physics principle is to select a fixed number of (e.g., 7) beam angles which are corresponding to the minimum index values on the map. In this example method, an additional term is introduced to take into account the combination effects of multiple beams. An additional energy term is added to the efficiency index which is inverse proportional to the angle separation between each pair of beams $\alpha_{ij}$. So the total energy is represented by:

$$E = EI(\alpha_i) + \sum_{i \neq j} \frac{k}{(1 - \cos\alpha_{ij})}$$

where EI is the beam efficiency index. The energy constant k represents the relative importance of beam separation to the minimization of EI.

For complex cases in which the PTV is large or consists of several sub-volumes, the size of each beam need to be adjusted by blocking part of the field in the beam's-eye-view ("blocking field" method) so that different beam bouquet settings can be used to treat different parts of the tumor. In such cases, the beam efficiency maps need to be calculated on each CT image slice individually to capture the change of anatomical features. The contiguous slices with similar efficiency map features can be grouped together. To ensure the continuity of slices in each group, a contiguity constraint cluster method can be used for the grouping. The collimator positions for beam blocking are then adjusted automatically to allow that different beam configurations can be applied to different slice groups.

When the features of prior patient data and beam efficiency index map are combined to learn the beam configuration process, the data-driven knowledge and physics principle-driven knowledge can be combined to present the best patient specific beam configuration.

With the prior patient's anatomy, treatment plan and physician's prescriptions are extracted into features to characterize their impact on the beam angle preferences, and with the beam efficiency index characterize and analyze the current patient's anatomy and physician's prescriptions, the presently disclosed beam angle model combines the prior data with current data for the best beam configuration of the new patient's need.

The predictive models described herein can be incrementally updated as new plans are generated. A network of plan databases from multiple treatment centers can be set up to enable efficient and large scale learning of the predictive models.

The selection of the incident angles of the treatment beams can be a critical component of IMRT planning for lung cancer cases. Efficient knowledge based automatic beam configuration determination methods and systems disclosed herein can utilize patient-specific anatomy and tumor geometry information and a beam bouquet atlas.

In embodiments disclosed herein, systems and methods are based on learning the relationship between patient anatomy and beam configurations from clinical plans designed by experienced planners. The training dataset contains 60 lung IMRT plans with tumor locations in the right lung, left lung, mediastinum and chest wall (26, 23, 8 and 3 cases, respectively) with plan prescription dose between 45 and 70 Gy.

An example method may include three major steps. First, a beam bouquet atlas can be established by classifying the clinical plans into 6 beam configuration groups using the k-medoids cluster analysis method. The beam arrangements in each medoid of the clusters can be designated as the standardized beam bouquet for the cluster. Second, a beam navigation map can be constructed to characterize the relative geometry of the tumor relative to the lungs, the body and the other OARs at each candidate beam direction. Finally, the beam navigation maps of the clinical cases and the cluster assignments of their beam bouquets were paired to train a Bayesian classification model. This classification model can be used to select a suitable beam bouquet from the atlas for a new case based on its beam navigation map.

This technique was validated by leave-one-out cross validation with 16 cases randomly selected from the original dataset. The dosimetric quality of the plans using the automatically determined beam bouquet (auto-beam plans) was evaluated against that of the corresponding clinical plans by a paired t-test.

As a result of the experiment, the dosimetric parameters (mean±S.D. in percentage of prescription dose) in the auto-beam plans and in the clinical plans, respectively, and the p-values by a paired t-test (in parenthesis) are: lung mean dose (Dmean): 16.3±9.3, 18.6±7.4 (0.48), esophagus Dmean: 28.4±18, 30.7±19.3 (0.02), Heart Dmean: 21.5±17.5, 21.1±17.2 (0.76), Spinal Cord $D_{2\%}$: 48±23, 51.2±21.8 (0.01), PTV dose homogeneity ($D_{2\%}$-$D_{99\%}$): 22±27.4, 20.4±12.8 (0.10). Overall, there are statistically significant dose reductions by the auto-beam plans in esophagus Dmean and cord $D_{2\%}$. However, the reductions which are <4% may not be clinically significant. This shows that plans generated by the automatic beam angle determination method can at least achieve dosimetric quality equivalent to that of clinical plans. This method can help improve the quality and efficiency of lung IMRT planning.

Figure 3:
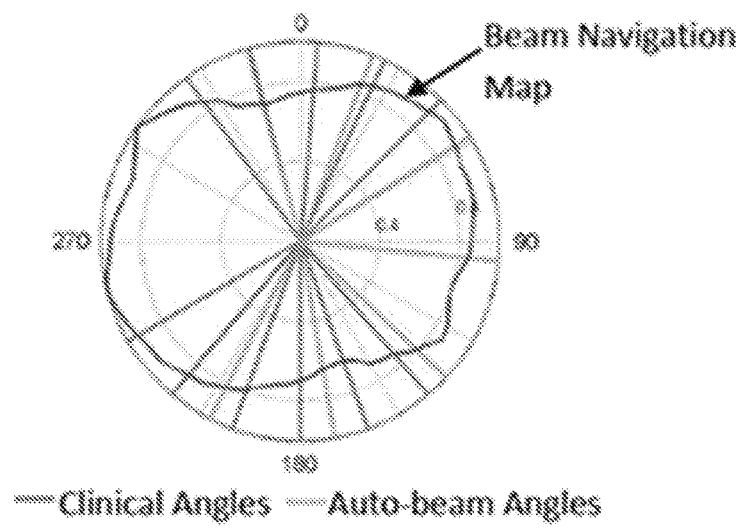
FIG. 3 illustrates a beam navigation map of case #16 (blue contour) is shown here as an example. The beam bouquet configurations of FIG. 3 are indicated as radial lines.
Figure 4:
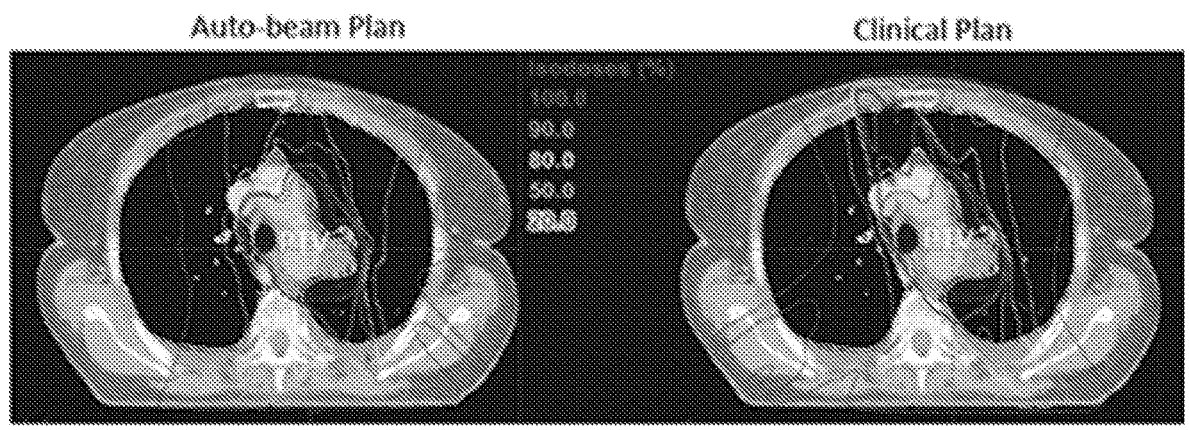
FIG. 4 illustrates a CT image and isodose lines for case #16 in the auto-beam and clinical plans.

FIG. 3 is a beam navigation map of case #16. The beam bouquet configurations are indicated as radial lines. FIG. 4 illustrates CT image and isodose lines in the auto-beam and clinical plans. Isodoses are depicted by greyscale.

Intensity modulated radiation therapy (IMRT) has demonstrated evidence as an effective technique for cancer treatment in the thorax with reduced toxicity. Due to variations in tumor location, tumor size and patient anatomy, selection of the incident angles of the treatment beams is a critical component of IMRT planning as it offers another dimension to maximize organ sparing. In clinical practice, beam angles are often selected based on the planner's experience and adjusted through a trial-and-error process to find an optimal set of beam bouquet.

Approaches to aid the selection of beam angles in IMRT planning have been reported. The beam angle optimization in IMRT planning is a large scale combinatorial optimization problem due to the large search space of possible beam angle combinations and the coupling of beam orientation optimization and the beam intensity optimization for each beam. In order to find the optimized beam angles within a clinically practical timeframe, these studies utilized a number of global optimization methods with consideration of time efficiency, including simulated annealing, the genetic algorithm, sparse optimization, and nested partition method. However, a significant amount of time is still required to perform the iterative beam angle optimization process using these methods. For example, two to a few hours of planning time for head-and-neck plans using un-optimized computing architectures has been reported.

Other studies approximated the combinatorial beam angle optimization problem by sequentially eliminating single candidate beam directions from the treatment plan or by adding one to the treatment plan in an iterative procedure. An automatic beam angle elimination method in an automatic lung IMRT planning process has been developed. In this method, the frequency distributions of the beam angles used for three major tumor locations (left, right and middle) are extracted from a set of prior plans. The 19 most frequently used beam angels are selected as initial angles for each tumor location. During beam intensity optimization, these beams are eliminated sequentially if it does not reduce the plan quality. In an example, starting from an empty plan with no beams selected, each not yet selected candidate beam direction is temporarily added to the plan during each iteration and the beam intensity optimization problem is solved. The process is stopped if adding more beams no longer improves plan quality.

Several studies have developed population-based beam bouquets (i.e., entire beam configuration settings) for certain treatment sites. In a study, beam bouquets with 3 to 9 beams for prostate IMRT planning were demonstrated by averaging the beam directions for all the patients under study. In another study, simulated annealing is used to classify a set of clinical liver plans into two beam bouquets, each with five beams.

In the present study, the feasibility of establishing a small set of standardized beam bouquets for lung IMRT planning was investigated. The bouquets were determined by learning the patterns from the multi-dimensional beam configuration features of prior clinical plans using a cluster analysis method. The validity of these bouquets was assessed by re-planning 20 clinical cases with these bouquets and evaluating the dosimetry against original clinical plans.

Sixty (60) lung IMRT plans with prescription doses ranging from 45 Gy to 70 Gy were retrospectively studied under an IRB approved research protocol. The plans have six to eleven co-planar beam angles, with an average beam number of eight. The dataset has a wide range of tumor size (from 12 to 4432 cm$^3$, mean 502 cm$^3$) and locations. The tumor locations in the dataset are distributed as follows: 26 cases in the right lung, 23 in the left lungs, 8 in the mediastinums and 3 in the chest walls.

An unsupervised cluster analysis method was used to classify the beam angle features of the training data to realize a set of standardized beam bouquets. The method can involve three major steps: 1) defining a dissimilarity measure between two beam bouquets, 2) determining a suitable number of clusters and classifying the beam angle settings using the k-medoids classification algorithm and finally, 3) establishing the standardized beam bouquets from the resulting clusters.

When defining the dissimilarity measure between two beam bouquets, a dissimilarity measure is defined between two beam bouquets. The dissimilarity measure is computed as the sum of angle separations between each pair of corresponding beams in the two bouquets. It takes into account the permutation of beams within each bouquet when comparing two beams. Specifically, a distance is first defined between two angles a and b, $$\delta(a, b) = \min_{k \in Z} |a - b + 360k|,$$

where k can take any value in the integer set Z and the 360k term accounts for the 360 degree modulo in the angle space. Then, the dissimilarity measure between two bouquets with the same number of beams $x_1 = (x_1^1, x_2^1, \ldots, x_n^1)$ and $x_2 = (x_1^2, x_2^2, \ldots, x_n^2)$ is defined as:

$$d^1(x_1, x_2) = \min_{\sigma \in \pi} \sum_{l=1}^{n} \delta(x_{\sigma(l)}^1, x_l^2),$$

where $\sigma$ is any permutation $\pi$ of the beam orders. In our dataset, the number of beams used in a plan ranges from 6 to 11, thus it is necessary to classify beam angle settings with different number of beams, by defining the dissimilarity measure between bouquets with different number of beams. If two bouquets $x_1$ and $x_2$ have different numbers of beams $n_1$ and $n_2$ and assume $n_1 > n_2$ without losing generality, we define the dissimilarity as the sum of two terms:

$$d(x_1, x_2) = \min_{x_1' \subseteq x_1} d^1(x_1', x_2) + \min_{x_2' \subseteq x_2} d^1(x_1 \setminus x_1', x_2'),$$

where $x_1'$ is a subset of $x_1$ which has the same number of beams as $x_2$ and $x_2'$ is a subset of $x_2$ with beam number $n_1 - n_2$. The first term compares $n_2$ beams in both $x_1$ and $x_2$ to calculate the distance, while the second term compares the remaining $n_1 - n_2$ beams in $x_1$ with $x_2$. This step ensures that every beam in the plan is taken into account when calculating the dissimilarity between two bouquets with different number of beams.

The dissimilarity needs to be evaluated between each of the two beam bouquets in the training dataset. The calculation of the dissimilarity involves the permutation of all beam angles in one configuration, which is equivalent to solving a Linear Assignment Problem (LAP). A fast algorithm for LAP, the Jonker-Volgenant algorithm may be used in this step to save the computation time.

Subsequently, standardized beam bouquets may be established. After the dissimilarity (or distance) may be calculated between each pair of the beam bouquets, a k-medoids method is used to sort the beam angle configurations into clusters. A medoid is defined as the object in a cluster, with the average distance to all the other objects in the same cluster (within-cluster distance) being the minimal. Thus, the medoid of a cluster is the most representative beam angle configuration of all cases within the cluster. The set of all medoids characterizes the major types of beam angle settings frequently used in clinical lung IMRT plans and they are designated as the standardized beam bouquets. The medoid case that corresponds to a standardized beam bouquet is designated as the reference case of this bouquet.

In the k-medoids method, the final classification result is dependent on the selection of k objects as the initial medoids to start the classification iteration. To avoid the iteration from being trapped in a local minimum, the classification procedure is repeated multiple times, beginning with a different set of randomly selected initial medoids at each time, to find the final medoids with the lowest sum of within-cluster distance.

A class solution needs to include sufficient number of beam bouquets in order to cover a wide variety of clinical cases with minimal error. On the other hand, the number of bouquets may not be too large so that the most suitable bouquet can be selected quickly and it is representative of certain clinical case characteristics. The appropriate number of beam bouquets were investigated by generating classifications with 3 to 8 clusters and calculating the average silhouette width $\bar{s}$ for each classification. In general, a higher average silhouette width value indicates better overall cluster separation in the classification.

The average silhouette width $\bar{s}$ is the average of the silhouette index s(i) over all the data points in the dataset. The silhouette index measures how close each point in one cluster is to the data points in the neighboring clusters. For a data point i in cluster A, let a(i) be the average distance of i to all other points in cluster A, d(i, C) be the average distance of i to all the data points in another cluster C. the silhouette index is defined as:

$$s(i) = 1 - \frac{a(i)}{\min_{C \neq A} d(i, C)}$$

The silhouette index s(i) has a numerical value from +1 to −1. Large positive value indicates the point in one cluster is far from neighboring clusters, while negative value indicates the point may be assigned to a wrong cluster. A silhouette plot can be used to visualize how well separated the resulting clusters are. It plots the silhouette index s(i) for each data point as a horizontal bar. A wider silhouette plot indicates larger s(i) values.

Subsequently, the standardized beam bouquets with clinical cases can be validated. Twenty (20) additional lung cancer cases randomly selected from the clinical dataset were re-planned to assess the validity of using the standardized beam bouquets. For each case, a planner experienced in routine clinical lung IMRT planning manually matched a standardized beam bouquet to the patient anatomy based on his/her judgment of the similarity between the tumor location and patient anatomical features of the case and those of the reference cases. The planner had no knowledge of (i.e., was blinded to) the beam configurations used in the original clinical plans. After the beam bouquet was selected, inverse planning/optimization was performed using the same dose objectives as in the clinical plans.

In some cases, the PTV is large or consists of several sub-volumes which are located at different parts of the lung. A "blocking field" method was used to manually block part of the field (i.e., only part of PTV is exposed) by adjusting collimator positions in the beam's-eye-view. This process mimics the routine clinical practice to spare critical organs such as heart in situations when tumor location changes in cranial-caudal direction. However, no adjustment to the beam angles was made once they had been selected from the standardized bouquets. The quality of the plans generated using the standard beam bouquets is evaluated by comparing the dosimetric parameters and DVHs of the bouquet-based plans with those of the original clinical plans. Paired t-tests were performed, with significance threshold set at 0.05.

To further evaluate the effect of the number of beam bouquets (i.e., the value of k) on plan quality, the 20 test cases were re-planned again using different numbers of bouquet options. The dosimetric quality of these plans was compared with those plans generated with the set of bouquets determined in the last section.

Figure 5A:
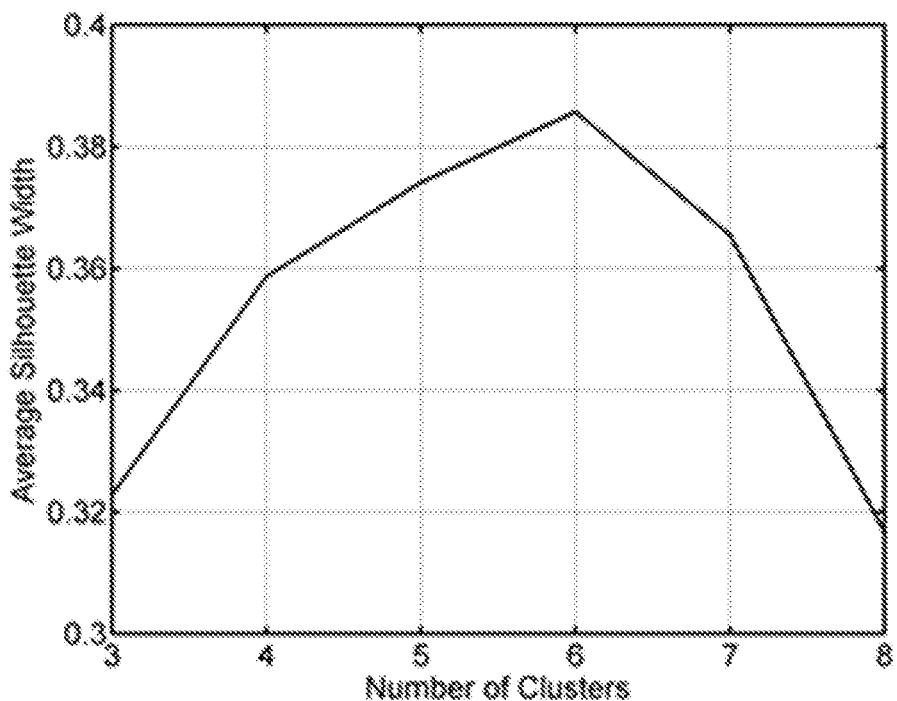
FIG. 5A illustrates an average silhouette width for the classifications with each given number of clusters.
Figure 5B:
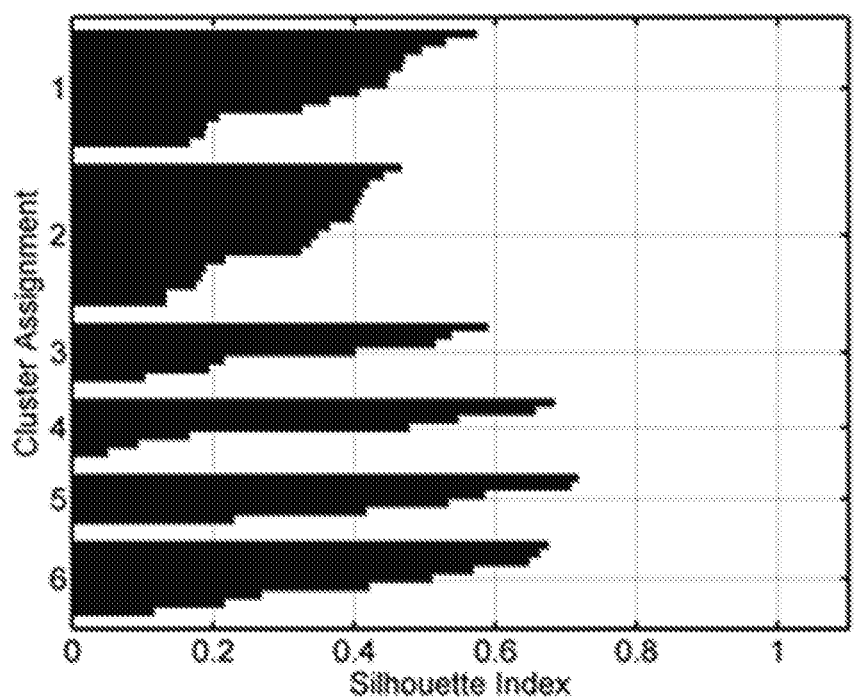
FIG. 5B illustrates a silhouette plot for the classifications with six clusters.

In an example, the beam settings in the training dataset were classified into 3 to 8 clusters by the k-medoids algorithm. The average silhouette width $\bar{s}$ for each classification result is plotted against the number of clusters in FIG. 5A. As shown in FIG. 5A, the classification with 6 clusters has the largest average silhouette width value of 0.39, which suggests that 6 bouquets best represent the beam configuration patterns in the dataset. The silhouette plot with 6 clusters is shown in FIG. 5B. The all positive silhouette index values indicate that the beam configurations align well within their assigned clusters. The beam bouquets corresponding to the medoids of the 6 clusters are shown in FIG. 2. The number of beams in these bouquets ranges from 7 to 9, which reflects the number of beams used in the reference clinical plans. The representative axial CT image slices of these reference plans are also shown under each medoid in FIG. 2. As shown, these beam configurations reflect the gross anatomical and tumor location characteristics. For example, bouquet #1 and #2 consist of two groups of beams coming mostly from the anterior and posterior directions, corresponding to cases in which the tumors are mainly in the middle of the lungs, while the other bouquets consist of beams mainly from one side of the body aiming to minimize the contra-lateral lung dose.

FIG. 5A illustrates the average silhouette width for the classifications with each given number of clusters. FIG. 5B illustrates the silhouette plot for classifications with six clusters. Each horizontal bar of FIG. 5B indicates the silhouette index for an object, which is grouped according to its cluster assignment. FIG. 5B also illustrates the width of each bar represent the silhouette index value. Each vertical axis of FIG. 5B numbers indicates the indices of the clusters.

Figure 6:
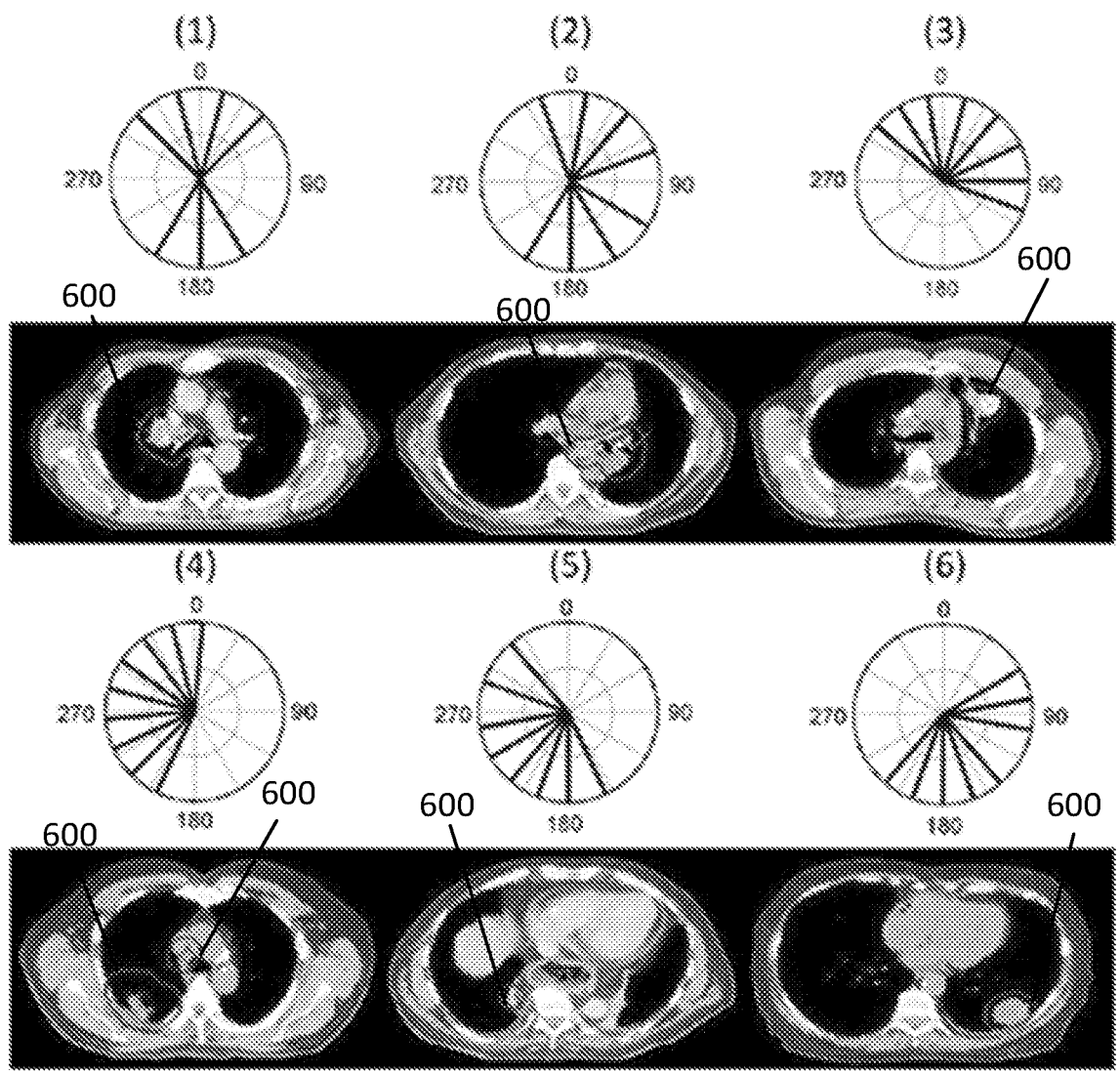
FIG. 6 illustrates six beam bouquets shown in polar coordinates using IEC beam angle convention at the first and third rows.

FIG. 6 illustrates six beam bouquets are shown in polar coordinates using IEC beam angle convention at the first and third rows. The solid radial lines indicate the beam directions. The number inside the parenthesis on top of each bouquet labels the ID of the bouquet. The representative axial CT image slices of the reference cases corresponding to the medoids of the 6 clusters are shown under each medoid at the second and fourth rows. The PTV is denoted by the red contours and the lung by the blue contours.

Figure 7:
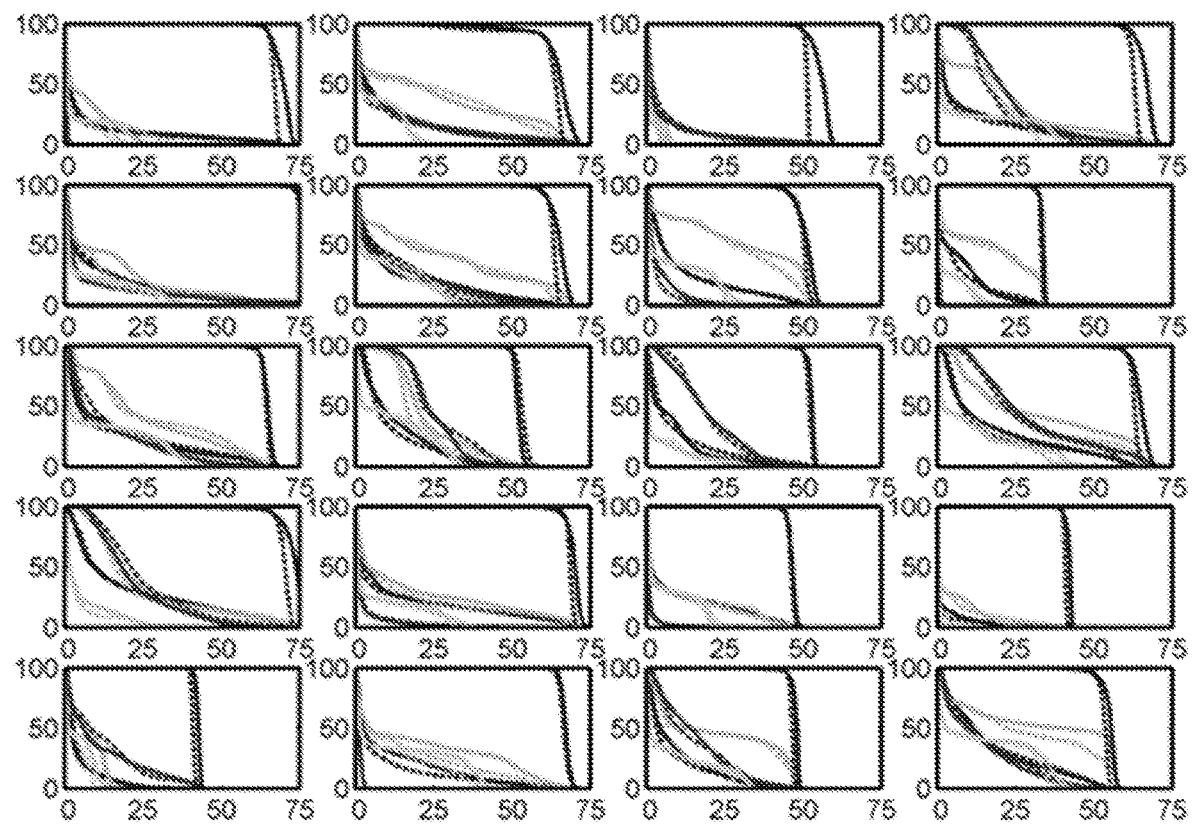
FIG. 7 illustrates a flowchart of an example method for automated radiation treatment with decision support in accordance with embodiments of the present disclosure.
Figure 8:
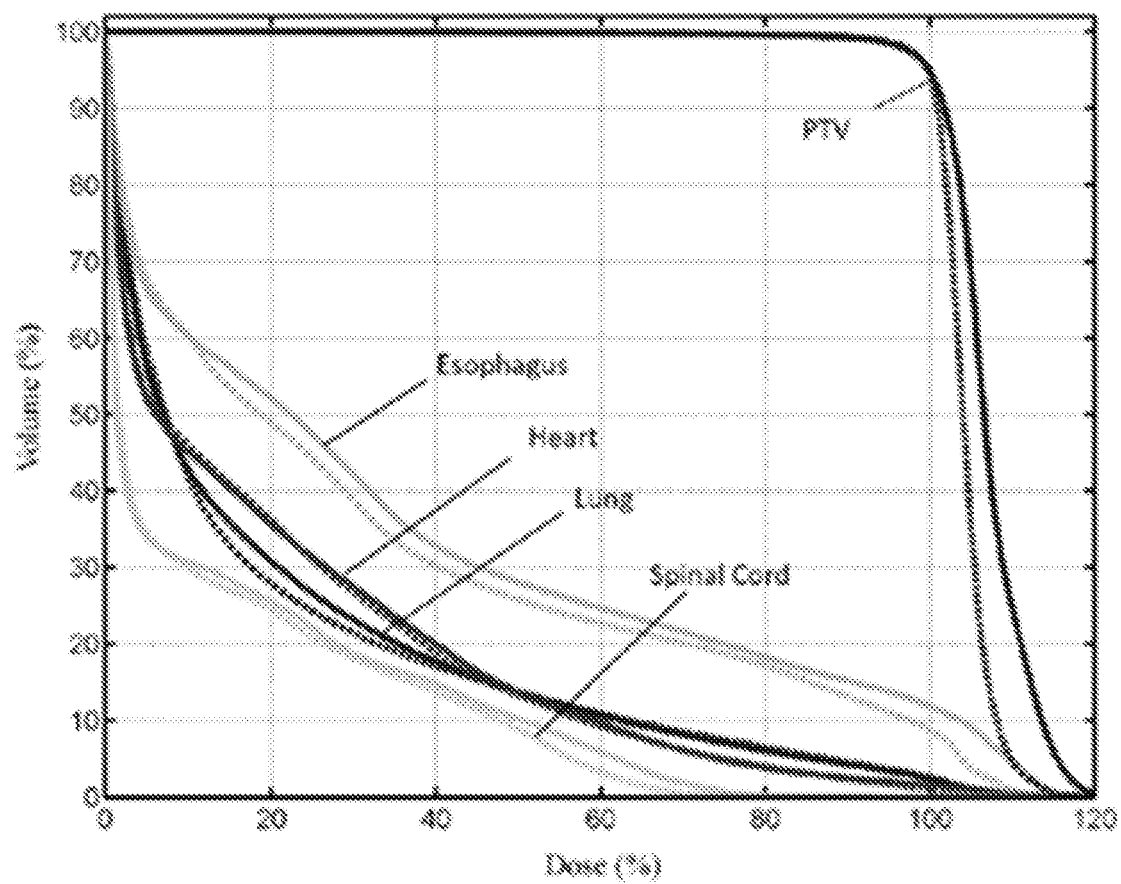
FIG. 8 illustrates a graph showing the means of the DVHs for the PTV and organs at risk (OARs) over all the validation cases.
Figure 9:
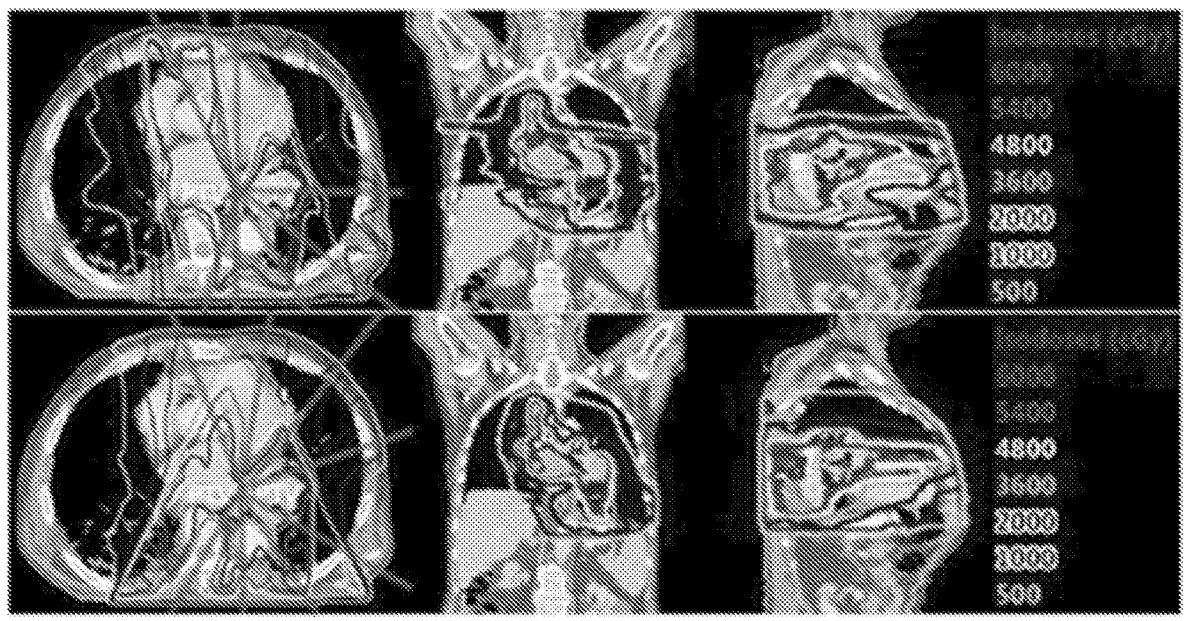
FIG. 9 images depicting the isodose lines in case #12 as shown on the representative axial, coronal and sagittal CT image slices.

The 20 validation cases were re-planned utilizing the standardized beam bouquets. The planner selected a bouquet for each case (with the tally listed in Table 1) by matching the reference cases' tumor location and patient anatomical characteristics with those of the validation case. In three of these plans: #11, #12 and #13, the jaws for some beams were adjusted to block part of the field. They were used mainly to reduce the dose to the heart when the beam directly passing through it. The DVHs for the PTV and the OARs in the standardized bouquet based plans and those in the clinical plans are plotted in FIG. 7, while the mean DVHs of all the validation cases are shown in FIG. 8. Example dose distributions in both bouquet-based and original clinical plans for case #12 are shown in FIG. 9. As is shown, the 100% isodose line in the bouquet-based plan appears to better conform to the PTV than the clinical plan on the axial CT slice. The lung in the bouquet-based plan appears to have better dose sparing than the clinical plan on the coronal slice, and vice versa in the sagittal slice. The overall dose sparing for the lung is comparable between the two plans, as shown by the DVH plots (FIG. 7).

Table 2 lists the mean and standard deviations of the dosimetric parameters in the bouquet-based and the clinical plans, as well as the paired t-test values. The lung $V_{10Gy}$, the esophagus mean dose, cord $D_{2\%}$ and PTV dose homogeneity defined as $D_{2\%}-D_{99\%}$ are statistically better in bouquet-based plans (p-value<0.05), but the improvements (<5%) were small and may not be clinically significant. Other dosimetric parameters are not statistically different.

TABLE 1

The IDs of the beam configuration bouquets which were chosen
by the planner to re-plan the 20 validation cases.

| Case ID | Bouquet ID |
|---|---|
| 1 | 5 |
| 2 | 1 |
| 3 | 3 |
| 4 | 6 |
| 5 | 3 |
| 6 | 1 |
| 7 | 1 |
| 8 | 2 |
| 9 | 5 |
| 10 | 2 |
| 11 | 2 |
| 12 | 2 |
| 13 | 5 |
| 14 | 1 |
| 15 | 4 |
| 16 | 1 |
| 17 | 3 |
| 18 | 1 |
| 19 | 1 |
| 20 | 1 |

As mentioned previously, FIG. 7 illustrates DVHs of the lung, esophagus, heart and spinal cord (as shown by the curves) in the plans which used the beam bouquet bouquets are compared with those in the clinical plans. The clinical plans are represented by the solid curves and the plans using bouquets by the dashed curves. The PTV DVHs are represented by the blue curves on the high dose end of the plots. The panels are ordered sequentially top-down and left-to-right according to the case IDs.

Also mentioned previously, FIG. 8 illustrates the means of the DVHs for the PTV and OARs over all the validation cases. The clinical plans are represented by the solid curves and the plans using bouquets by the dashed curves. FIG. 9 illustrates the isodose lines in case #12 are shown on the representative axial, coronal and sagittal CT image slices. The magenta lines indicate beam directions. Top row: clinical plan, bottom row: plan using beam angle bouquet. The prescription dose to the PTV is 60 Gy.

Table 2 shown below demonstrates mean and standard deviations (S.D.) of the dosimetric parameters in plans using 6 beam bouquets and those in the clinical plans. They are compared by paired t-tests.

| OAR/PTV | Parameter | Plans using bouquets Mean ± S.D | Clinical plans Mean ± S.D | p-value |
|---|---|---|---|---|
| Lung | $V_{10\ Gy}$ (% OAR volume) | 29.1 ± 11.7 | 32 ± 12.6 | 0.01 |
| | $V_{20\ Gy}$ (% OAR volume) | 18.3 ± 8.1 | 18.9 ± 8.7 | 0.44 |
| | Mean dose (% Dx) | 18.8 ± 7.0 | 19.2 ± 7.0 | 0.28 |
| Esophagus | Mean dose (% Dx) | 32.0 ± 16.3 | 34.4 ± 17.9 | 0.01 |
| Heart | $V_{60\ Gy}$ (% OAR volume) | 0.6 ± 1.1 | 1.2 ± 2.7 | 0.39 |
| | Mean Dose (% Dx) | 19.2 ± 16.5 | 19.4 ± 16.6 | 0.74 |
| Spinal Cord | $D_{2\%}$ (% Dx) | 47.7 ± 18.8 | 52.0 ± 20.3 | 0.01 |
| PTV | $D_{2\%}$-$D_{99\%}$ (% Dx) | 17.1 ± 15.4 | 20.7 ± 12.2 | 0.03 |

Abbreviations:
OAR: organ at risk,
PTV: planning target volume,
Dx: prescription dose,
S.D.: standard deviation,
$V_{xGy}$: portion of OAR volume irradiated by dose higher than x Gy,
$D_{x\ \%}$: maximum dose covering at least x % of OAR volume In order to evaluate whether more standardized beam bouquets would further improve planning and fewer would deteriorate the plan quality, beam bouquets for the 5-bouquet and 7-bouquet options were determined by the classification algorithm using the number of clusters as 5 and 7, respectively. The results showed remarkable stability in the final classification. Careful inspection of the resulting medoids revealed that the only difference between the 6 bouquet and 7 bouquet options is the addition of one more beam bouquet choice in the 7 bouquet option, while the six other bouquet choices are identical. Similarly, the only change in the 5 bouquet option is that there is one beam bouquet choice that is eliminated from the 6 bouquets.

The same 20 validation cases were planned again using 5 and 7 standardized beam bouquets. Among all 20 cases, only in 3 cases (#4, #16, #17) different beam bouquets were chosen by the planner when the bouquet options were switched from 6- to 5-bouquet and from 6- to 7-bouquet. The dosimetric parameters in these cases are listed in Table 3. As shown, when the number of bouquets is changed from 7 to 6, there is no significant change in the dosimetric parameters. When the number of bouquets is further decreased from 6 to 5, the lung $V_{5Gy}$ and the mean heart dose in case #4 are increased significantly.

Table 3 below provides a comparison of the dosimetric parameters in the plans which used beam configurations chosen from 5-, 6- and 7-bouquet options. The cases listed in Table 3 are those for which different beam configurations were chosen when switching between different options.

TABLE 3

| | OAR/PTV | | | | | | | | | | |
|---|---|---|---|---|---|---|---|---|---|---|---|
| | Lung | | | | Esophagus | | | Heart | | Cord | PTV |
| Parameter | $V_{5\ Gy}$ | $V_{10\ Gy}$ | $V_{20\ Gy}$ | $D_{mean}$ | $V_{20\ Gy}$ | $V_{60\ Gy}$ | $D_{mean}$ | $V_{60Gy}$ | $D_{mean}$ | $D_{2\%}$ | $D_{2\%}$-$D_{99\%}$ |
| Case #16 | | | | | | | | | | | |
| 7 Bouquet | 7.3 | 4.9 | 2.6 | 3.9 | 9.3 | 0.0 | 11.2 | 0.0 | 0.0 | 12.1 | 5.3 |
| 6 Bouquet | 6.7 | 4.9 | 3.5 | 4.1 | 8.2 | 0.0 | 10.8 | 0.0 | 0.0 | 11.8 | 5.5 |
| Case #17 | | | | | | | | | | | |
| 7 Bouquet | 29.2 | 16.4 | 6.7 | 13.1 | 2.4 | 0.0 | 20.2 | 0.0 | 29.1 | 31.9 | 8.8 |
| 6 Bouquet | 24.0 | 12.1 | 4.4 | 11.2 | 0.0 | 0.0 | 17.9 | 0.0 | 30.0 | 23.7 | 7.4 |

TABLE 3-continued

| | OAR/PTV | | | | | | | | | | |
|---|---|---|---|---|---|---|---|---|---|---|---|
| | Lung | | | | Esophagus | | | Heart | | Cord | PTV |
| Parameter | $V_{5\,Gy}$ | $V_{10\,Gy}$ | $V_{20\,Gy}$ | $D_{mean}$ | $V_{20\,Gy}$ | $V_{60\,Gy}$ | $D_{mean}$ | $V_{60Gy}$ | $D_{mean}$ | $D_{2\%}$ | $D_{2\%}$-$D_{99\%}$ |
| Case #4 | | | | | | | | | | | |
| 6 Bouquet | 32.0 | 24.5 | 17.4 | 15.6 | 37.4 | 3.0 | 29.3 | 0.0 | 31.0 | 54.9 | 9.9 |
| 5 Bouquet | 37.3 | 25.3 | 16.2 | 15.8 | 40.5 | 2.8 | 29.6 | 0.0 | 35.3 | 57.7 | 10.5 |

Abbreviations:
OAR: organ at risk,
PTV: planning target volume,
$V_{x\,Gy}$: portion of OAR volume irradiated by dose higher than x Gy (Unit: percentage of OAR volume),
$D_{x\%}$: maximum dose covering at least x % of OAR volume (Unit: percentage of prescription dose).
$D_{mean}$: mean dose (Unit: percentage of prescription dose).
5, 6 or 7 Bouquet: plans using beam configurations chosen from 5, 6 or 7 bouquet options, respectively.

In this study, six bouquets were determined as the standardized beam bouquets to characterize the major types of beam angle settings used in clinical plans based on the average silhouette value. Validation test was performed by re-planning 20 clinical cases with these bouquets. The effect of the number of beam bouquets on plan quality were further evaluated by planning the 20 cases using 5 and 7 bouquets. It was found that the quality of the plans was not affected when the number of bouquets changed from 7 to 6, while the OARs would receive significantly higher dose in one of the test plan if the bouquet number was further reduced to 5. This exercise confirms that for the limited size of the dataset, the six beam angle bouquet option provides a good balance of plan quality and number of bouquets in lung IMRT planning. However, since the 7 bouquet option only adds one bouquet while keeping the other 6 bouquets identical to the 6 bouquet option, it will be a simple extension if additional clinical case complexity warrants more bouquet options in the future.

The number of beams used in the standardized bouquets ranges from 7 to 9. It reflects the variation of the number of treatment beams used in the clinical plans. It may be desirable to further standardize these bouquets by adopting equal number of beams, e.g. 7 beams in each bouquet. One approach to standardize these bouquets is to combine neighboring beams in the 8-beam and 9-beam plans. Further study is needed to determine the best approach for such standardization.

The beam bouquets contain only coplanar angles as only the clinical plans using coplanar beam angles were included in the training dataset. It has been shown that non-coplanar beam angles can further improve the quality of the IMRT and SBRT plans for lung cancer treatment. In clinical practice, because of the difficulty of determining the appropriate non-coplanar beam angles and additional treatment setup time associated with the couch rotation and the risk of gantry-couch collision, non-coplanar beam angles are used less frequently and are often reserved for cases with complicated tumor geometries and patient anatomy.

In this study, although the beam bouquets were learned from a set of clinical plans from a single institution, the cases in the dataset cover a wide range of tumor location, tumor volume and patient anatomy. These plans were generated by multiple experienced dosimetrists and physicists for clinical treatment in our institution and have met all the physician's dose constraint prescriptions. Hence the dataset represents the general clinical practice and knowledge of beam selection in lung IMRT planning. These bouquets represent general clinical beam angle preferences and the standardization may help improve the efficiency and quality consistency for lung IMRT planning. Using the 20 clinical cases, it was shown that the plans generated with these bouquets have dosimetric qualities comparable to their manually generated clinical counterparts.

In order to simplify the plan quality comparison in this study, adjustment to the beam angles in the validation plans were not allowed. However in clinical applications, minor adjustments to the beam angles around the bouquet directions can be made in order to further improve the dosimetry of the plan, thus the bouquets can be used as a near optimal starting point and can be fine-tuned with other local beam angle optimization methods. Further, the beam bouquet for a validation case is matched manually by comparing the anatomical features of the validation case with those of the reference cases.

After the beam configurations are determined, the fluence map or MLC segments for each individual beam need to be optimized in the IMRT planning process based on a set of dose coverage and dose sparing objectives. Methods to automatically determine patient specific dose objectives in IMRT plans have been reported. A fully automatic planning method for lung IMRT plans can be developed by combining the automatic beam angle selection method with the automatic determination of dose objectives.

Figure 10:
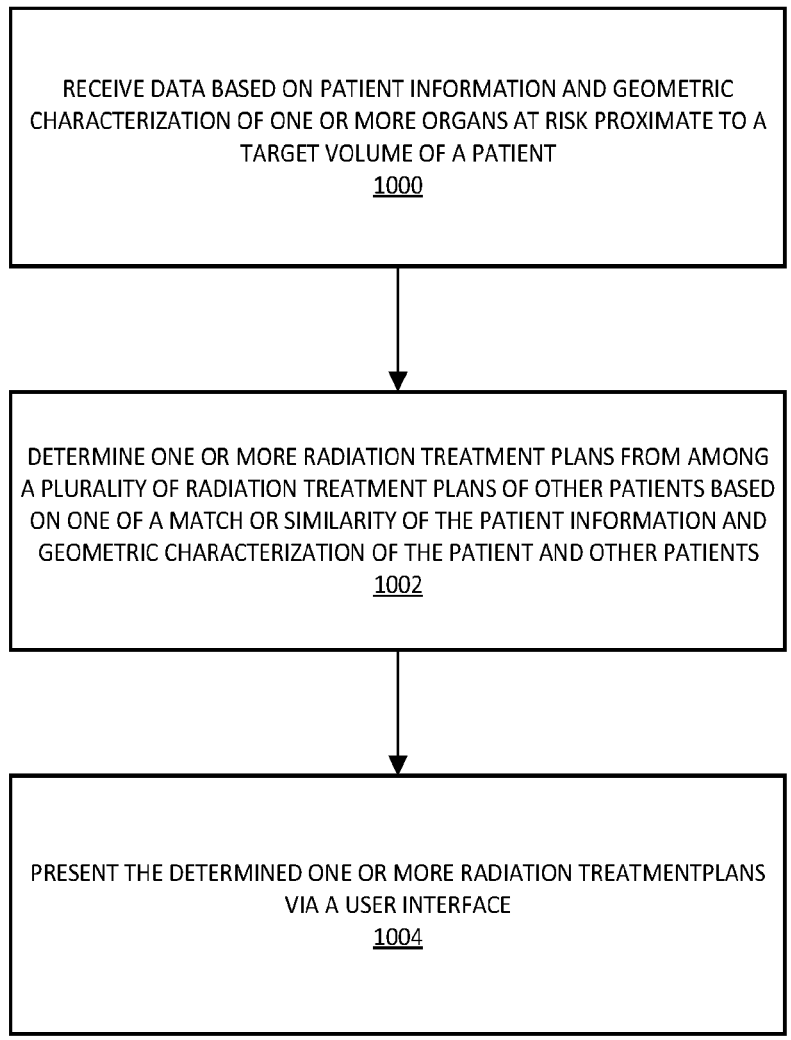
FIG. 10 illustrates a flowchart of an example method for automated radiation treatment with decision support in accordance with embodiments of the present disclosure.

FIG. 10 illustrates a flowchart of an example method for automated radiation treatment with decision support in accordance with embodiments of the present disclosure. The method may be implemented by any suitable computing device. Example computing devices include, but are not limited to, desktop computers, laptop computers, tablet computers, smartphone, and the like. A computing device may include one or more processors and memory configured to implement the function of this example method. Further, the computing device may include one or more user interfaces such as, but not limited to, a display, a keyboard, a mouse, and the like.

Referring to FIG. 10, the method includes receiving 1000 data based on patient information and geometric characterization of one or more organs at risk proximate to a target volume of a patient. For example, the patient information may include, but is not limited to, patient image, patient organ contour information, target volume contour information, clinical parameters, and the like. Further, patient information may include previous radiation treatment of the patient, previous treatment dose of the patient, location of previous radiation treatment of the patient, dose volume information of previous treatment dose of the patient, and physiological condition of the patient. In another example, patient information includes organ function analysis and/or transplant condition of the patient.

The method of FIG. 10 includes determining 1002 one or more radiation treatment plans from among a plurality of radiation treatment plans of other patients based on one of a match or similarity of the patient information and geometric characterization of the patient and the other patients. A radiation treatment plan may include a pattern of beam angles and dosage for use in treating a patient. Dosage information may include voxel-level dose information. In an example, a radiation treatment plan may be adjusted based on application of a beam to a critical structure such as, but not limited to, a spinal cord and/or organ at risk.

The method of FIG. 10 includes presenting 1004 the determined one or more radiation treatment plans via a user interface. For example, a computing device may present a radiation treatment plan via a display. As an example, a radiation treatment plan may define one or more of dose distribution and a dose volume histogram.

It is noted that the selection of the incident angles of the treatment beams can be a critical component of intensity modulated radiation therapy (IMRT) planning for lung cancer due to significant variations in tumor location, tumor size and patient anatomy. In a study, the feasibility of establishing a small set of standardized beam bouquets for planning is investigated. In the study, the set of beam bouquets were determined by learning the beam configuration features from 60 clinical lung IMRT plans designed by experienced planners. A k-medoids cluster analysis method was used to classify the beam configurations in the dataset. The appropriate number of clusters was determined by maximizing the value of average silhouette width of the classification. Once the number of clusters had been determined, the beam arrangements in each medoid of the clusters were designated as the standardized beam bouquet for the cluster. This standardized bouquet set was used to re-plan 20 cases randomly selected from the clinical database. The dosimetric quality of the plans using the beam bouquets was evaluated against the corresponding clinical plans by a paired t-test. The classification with 6 clusters has the largest average silhouette width value and hence would best represent the beam bouquet patterns in the dataset. The results showed that plans generated with a small number of standardized bouquets (e.g. 6) have comparable quality to that of clinical plans. These standardized beam configuration bouquets can help improve plan efficiency and facilitate automated planning.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

REFERENCES

Abraham, C., N. Molinari and R. Servien (2013). "Unsupervised clustering of multivariate circular data." *Statistics in Medicine* 32(8): 1376-1382.

Bangert, M. and U. Oelfke (2010). "Spherical cluster analysis for beam angle optimization in intensity-modulated radiation therapy treatment planning." *Phys Med Biol* 55(19): 6023-6037.

Breedveld, S., P. R. Storchi, P. W. Voet and B. J. Heijmen (2012). "iCycle: Integrated, multicriterial beam angle, and profile optimization for generation of coplanar and non-coplanar IMRT plans." *Med Phys* 39(2): 951-963.

Das, S., T. Cullip, G. Tracton, S. Chang, L. Marks, M. Anscher and J. Rosenman (2003). "Beam orientation selection for intensity-modulated radiation therapy based on target equivalent uniform dose maximization." *Int J Radiat Oncol Biol Phys* 55(1): 215-224.

Jia, X., C. Men, Y. Lou and S. B. Jiang (2011). "Beam orientation optimization for intensity modulated radiation therapy using adaptive 1(2,1)-minimization." *Phys Med Biol* 56(19): 6205-6222.

Li, Y., J. Yao and D. Yao (2004). "Automatic beam angle selection in IMRT planning using genetic algorithm." *Phys Med Biol* 49(10): 1915-1932.

Meyer, J., S. M. Hummel, P. S. Cho, M. M. Austin-Seymour and M. H. Phillips (2005). "Automatic selection of non-coplanar beam directions for three-dimensional conformal radiotherapy." *Br J Radiol* 78(928): 316-327.

Potrebko, P. S., B. M. C. McCurdy, J. B. Butler and A. S. El-Gubtan (2008). "Improving intensity-modulated radiation therapy using the anatomic beam orientation optimization algorithm." *Medical Physics* 35(5): 2170.

Pugachev, A., J. G. Li, A. L. Boyer, S. L. Hancock, Q. T. Le, S. S. Donaldson and L. Xing (2001). "Role of beam orientation optimization in intensity-modulated radiation therapy." *Int J Radiat Oncol Biol Phys* 50(2): 551-560.

Pugachev, A. and L. Xing (2001). "Pseudo beam's-eye-view as applied to beam orientation selection in intensity-modulated radiation therapy." *Int J Radiat Oncol Biol Phys* 51(5): 1361-1370.

Rocha, H., J. M. Dias, B. C. Ferreira and M. C. Lopes (2013). "Beam angle optimization for intensity-modulated radiation therapy using a guided pattern search method." *Phys Med Biol* 58(9): 2939-2953.

Schreibmann, E. and L. Xing (2004). "Feasibility study of beam orientation class-solutions for prostate IMRT." *Medical Physics* 31(10): 2863.

Schreibmann, E. and L. Xing (2005). "Dose-volume based ranking of incident beam direction and its utility in facilitating IMRT beam placement." *Int J Radiat Oncol Biol Phys* 63(2): 584-593.

Sheng, K., P. Dong, P. Lee, D. Ruan, T. Long, E. Romeijin, D. Low, P. Kupelian and Y. Yang (2013). "4π Non-Coplanar SBRT for Centrally Located or Larger Lung Tumors."*International Journal of Radiation Oncology\*Biology\*Physics* 87(2): S122.

Wang, X., X. Zhang, L. Dong, H. Liu, M. Gillin, A. Ahamad, K. Ang and R. Mohan (2005). "Effectiveness of noncoplanar IMRT planning using a parallelized multiresolution beam angle optimization method for paranasal sinus carcinoma." *Int J Radiat Oncol Biol Phys* 63(2): 594-601.

Zhang, H. H., S. Gao, W. Chen, L. Shi, W. D. D'Souza and R. R. Meyer (2013). "A surrogate-based metaheuristic global search method for beam angle selection in radiation treatment planning." *Phys Med Biol* 58(6): 1933-1946.

Zhang, X., X. Li, E. M. Quan, X. Pan and Y. Li (2011). "A methodology for automatic intensity-modulated radiation treatment planning for lung cancer." *Physics in Medicine and Biology* 56(13): 3873.

Potrebko, P. S., et al., A simple geometric algorithm to predict optimal starting gantry angles using equiangular-spaced beams for intensity modulated radiation therapy of prostate cancer. *Medical Physics,* 2007. 34(10): p. 3951.

Yuan, L., et al., Standardized beam bouquets for lung IMRT planning. Phys. Med. Biol., 2015.

Kaufman, L. and P. J. Rousseeuw, Finding Groups in Data. 2009, Hoboken, N.J.: John Wiley & Sons, Inc.

Kung, S. Y., Kernel methods and machine learning. 2014, *Cambridge University Press*. p. 1 online resource (pages cm.).

What is claimed:

1. A method comprising:
    receiving, at a computing device including a processor and memory, data based on patient information and geometric characterization of one or more organs at risk proximate to a target volume of a patient;
    constructing, by the processor, any one of a beam navigation map and beam efficient index:
    determining, by the processor, automatically one or more radiation treatment beam configuration sets by integrating a plurality of models learned from a plurality of prior plans and formulas based on physical principles using any one of the constructed beam navigation map and beam efficient index; and
    presenting, by the processor, the determined one or more radiation beam configuration sets via a user interface.

2. The method of claim 1, wherein the patient information includes one or more of patient image, patient organ contour information, target volume contour information, and clinical parameters.

3. The method of claim 1, wherein the one or more radiation beam configuration sets each include a pattern of beam angles, and wherein the plurality of prior plans comprises presenting information about the pattern of beam angles of the one or more radiation beam configuration sets.

4. The method of claim 1, wherein the wherein the one or more radiation beam configuration sets each include beam dosage information, and
    wherein presenting the determined one or more radiation beam configuration sets comprises presenting the beam dosage information of the one or more radiation beam configuration sets.

5. The method of claim 1, wherein the patient information includes one of previous radiation treatment of the patient, previous treatment dose of the patient, location of previous radiation treatment of the patient, dose volume information of previous treatment dose of the patient, physiological condition of the patient, patient preference, treatment goals.

6. The method of claim 1, wherein the patient information includes one of organ function analysis and transplant condition of the patient.

7. The method of claim 1, further comprising:
    receiving selection of one of the determined one or more radiation beam configuration sets via the user interface;
    receiving input for adjusting the selected one of the determined one or more radiation beam configuration sets via the user interface; and
    adjusting the selected one of the determined one or more radiation beam configuration sets based on the input.

8. The method of claim 1, wherein the geometric characterization associates each of a plurality of distances from the target volume with a respective percentage for a volume of the one or more organs at risk.

9. The method of claim 1, wherein the data comprises the size and shape of the target volume and the respective sizes and shapes of the one or more organs at risk.

10. The method of claim 1, wherein the data comprises information about one of radiation treatment knowledge, experience, preferences, computerized models of published clinical trials results and guidelines.

11. The method of claim 1, wherein the radiation beam configuration sets define at least one of a dose distribution and a dose volume histogram.

12. A method comprising:
    receiving, at a computing device including a processor and memory, data based on patient information and geometric characterization of one or more organs at risk proximate to a target volume of a patient;
    constructing, by the processor, any one of a beam navigation map and beam efficient index;
    determining, by the processor, automatically, one or more radiation treatment beam configuration sets by integrating a plurality of models learned from a plurality of prior plans and formulas based on physical principles using any one of the constructed beam navigation map and beam efficient index, wherein the one or more radiation treatment beam configuration sets comprises a set of beam bouquets;
    learning, by the processor, a best set of beam bouquets from the plurality of prior plans using a clustering technique; and
    presenting, by the processor, the determined one or more radiation beam configuration sets via a user interface.

13. The method of claim 12, wherein the clustering technique comprises k-medoid clustering.

14. The method of claim 12, wherein the set of beam bouquets are six or less in number.

15. A system comprising:
    at least one processor and memory configured to:
    receive data based on patient information and geometric characterization of one or more organs at risk proximate to a target volume of a patient;
    construct any one of a beam navigation map and beam efficient index;
    determine one or more radiation beam configuration sets from among a plurality of radiation beam configuration sets of prior patient cases based on one of a match or similarity of the patient information and geometric characterization of the patient and a plurality of radiation treatment plans from a plurality of prior patient cases and by an integration of a plurality of models learned from a plurality of prior plans and formulas based on physical principles using any one of the constructed beam navigation map and beam efficient index; and
    a user interface configured to present the determined one or more radiation beam configuration sets.

16. The system of claim 15, wherein the plurality of radiation beam configuration sets are each associated with data indicating patient anatomy,
    wherein the at least one processor and memory configured to:
    analyze the data indicating patient anatomy to generate mathematically parameterized patterns; and
    use the patterns to match the patient with one or more of the other patients, wherein the plurality of radiation treatment plans are the radiation beam configuration sets of the matched one or more of the plurality of prior patient cases.

17. The system of claim 15, wherein the plurality of radiation beam configuration sets each include a pattern of beam angles, and wherein the user interface is configured to present information about the pattern of beam angles of the one or more radiation beam configuration sets.

18. The system of claim 15, wherein the plurality of radiation beam configuration sets each include beam dosage information, and
wherein the user interface is configured to present the beam dosage information of the one or more radiation beam configuration sets.

19. The system of claim 18, wherein the beam dosage information includes voxel-level dose information.

20. The system of claim 18, wherein the at least one processor and memory configured to adjust the one or more radiation beam configuration sets based on application of a beam dose to a critical structure.

21. The system of claim 20, wherein the critical structure comprises one of a spinal cord and organ at risk.

22. A system comprising:
at least one processor and memory configured to:
 receive data based on patient information and geometric characterization of one or more organs at risk proximate to a target volume of a patient;
 determine one or more radiation beam configuration sets from among a plurality of radiation beam configuration sets of prior patient cases based on one of a match or similarity of the patient information and geometric characterization of the patient and the prior patient cases,
 wherein the determined radiation beam configuration sets comprise a set of beam bouquets;
 determine a best set of beam bouquets from a plurality of prior plans based on a clustering technique; and
a user interface configured to present the determined one or more radiation beam configuration sets.

* * * * *